United States Patent
Fine et al.

(10) Patent No.: US 6,587,704 B1
(45) Date of Patent: Jul. 1, 2003

(54) METHOD FOR NON-INVASIVE OPTICAL MEASUREMENTS OF BLOOD PARAMETERS

(75) Inventors: Ilya Fine, Rehovot (IL); Leonid Shvartsman, Jerusalem (IL)

(73) Assignee: Orsense Ltd., Tirat Hacarmel (IL)

( * ) Notice: Subject to any disclaimer, the term of this patent is extended or adjusted under 35 U.S.C. 154(b) by 0 days.

(21) Appl. No.: 09/652,350

(22) Filed: Aug. 31, 2000

Related U.S. Application Data

(63) Continuation-in-part of application No. 09/468,178, filed on Dec. 21, 1999, now Pat. No. 6,400,972, which is a continuation of application No. PCT/IL99/00331, filed on Jun. 16, 1999.

(51) Int. Cl.$^7$ .................................................. A61B 5/00
(52) U.S. Cl. ........................ 600/335; 600/322; 600/316
(58) Field of Search ........................ 600/309–311, 316, 600/327, 322–326, 335; 356/39–42

(56) References Cited

U.S. PATENT DOCUMENTS

| | | | |
|---|---|---|---|
| 4,201,470 A | * 5/1980 | Ehrly et al. | .................... 356/39 |
| 4,463,762 A | 8/1984 | Rubens | |
| 4,883,055 A | 11/1989 | Merrick | |
| 4,927,264 A | 5/1990 | Shiga et al. | |
| 4,975,581 A | * 12/1990 | Robinson et al. | ...... 250/339.09 |
| 5,054,487 A | * 10/1991 | Clarke | ......................... 600/316 |
| 5,057,695 A | * 10/1991 | Hirao et al. | ................ 250/575 |
| 5,069,214 A | * 12/1991 | Samaras et al. | ............ 600/323 |
| 5,638,816 A | 6/1997 | Kiani Azarbayjany et al. | |
| 5,810,734 A | * 9/1998 | Caro et al. | .................. 600/485 |
| 5,827,181 A | * 10/1998 | Dias et al. | .................. 600/322 |
| 5,931,779 A | 8/1999 | Arakaki et al. | |
| 6,222,189 B1 | * 4/2001 | Misner et al. | ........... 250/341.1 |
| 6,400,972 B1 | * 6/2002 | Fine | ........................... 600/322 |

FOREIGN PATENT DOCUMENTS

| WO | WO 98/17174 | 4/1998 |
|---|---|---|
| WO | WO 00/09004 | 2/2000 |

OTHER PUBLICATIONS

International Search Report for PCT/IL 99/00695 dated Sep. 8, 2000.
John M. Steinke, A.P. Shepherd, "Role of Light Scattering in Spectrophotometric Measurements of Arteriovenous Oxygen Difference", IEEE Trans., vol. BME–33, No. 8, Aug. 1986, p. 729–734.
Akira Ishimaru, "Wave Preparation and Scattering Random Media", vol. 1–2, Academic Press, New York, 1978.

* cited by examiner

*Primary Examiner*—Eric F. Winakur
*Assistant Examiner*—Matthew Kremer
(74) *Attorney, Agent, or Firm*—Fitch, Even, Tabin & Flannery

(57) ABSTRACT

A non-invasive method of optical measurements is presented for determining at least one desired parameter of patient's blood. The method utilizes reference data indicative of the values of the desired blood parameter as a function of at least two measurable parameters. At least one of the measurable parameters is derived from scattering spectral features of the medium highly sensitive to patient individuality, and the at least one other measurable parameter is indicative of artificial kinetics of the optical characteristics of the patient's blood perfused fleshy medium. A condition of artificial kinetics is created at a measurement location, and maintained during a certain time. Measurements are carried out with different wavelengths of incident light during a time period including this certain time. Measured data is in the form of time evolutions of light responses of the medium corresponding to the different wavelengths. By analyzing the measured data, the at least two measurable parameters are extracted, and the reference data is utilized to determine the at least one desired blood parameter.

27 Claims, 8 Drawing Sheets ize the implementation of pulse oximetry signals as carried
METHOD FOR NON-INVASIVE OPTICAL MEASUREMENTS OF BLOOD PARAMETERS This application is a continuation-in-part of U.S. application Ser. No. 09/468,178, filed Dec. 21, 1999, now U.S. Pat. No. 6,400,972, issued Jun. 4, 2002, which is a continuation of International Application. No. PCT/IL99/00331, filed on Jun. 16, 1999.

FIELD OF THE INVENTION

This invention is in the field of non-invasive optical measuring techniques, and relates to a method for determining parameters of the patient's blood.

BACKGROUND OF THE INVENTION

Optical methods for determining blood parameters include spectrophotometric measurements, which enable the indication of the presence of various blood constituents, based on the knowledge of their spectral behavior. These methods being applied in real medicine rather than in analytical chemistry create the basis for non-invasive (in vivo) blood tests, which present, no doubt, one of today's most exciting challenges. To make blood tests low-cost, safe and painless means to make them non-invasive.

The two main challenges, that any non-invasive optical method has to deal with, are as follows: (1) the low signal-to-noise ratio, and, (2) the large variability of individual parameters influencing the signal of concrete patients.

The main field in which the red-infrared (NIR) spectroscopy became the most widely recognized tool is the non-invasive monitoring of blood oxygenation. A pulse oximeter is the generally accepted standard of everyday clinical practice. It utilizes the so-called "AC measurement technique" which focuses on measuring only the "blood signal" of a blood perfused tissue illuminated by a predetermined range of wavelengths.

The operation of a pulse oximeter generally consists of the following: Light passing through the patient's finger comes out modulated by the waveform of his heartbeats. The amplitudes of this modulation for different light wavelengths contain information on the oxygen content in blood. Hence, a pulsatile component of the optical signal obtained from blood perfused tissue is utilized for determining the arterial blood oxygen saturation. In other words, the difference in light absorption of the tissue measured during the systole and the diastole phases is considered to be caused by blood that is pumped into the tissue during the systole phase from arterial vessels, and therefore has the same oxygen saturation as in the central arterial vessels.

Hence, for the AC signal, arterial blood plays the role of the key absorber. The spectral behaviors of Hb and $HbO_2$ absorbtion differ strongly, so the oxygen saturation can be extracted from the results of the measurements. To summarize the implementation of pulse oximetry signals as carried out today, it presents oximetry as an absorption-related method based on the convolution of natural kinetics (AC/DC ratio is analysed) and spectrophotometric behavior of various ingredients. The generic limitations of this method are as follows: First, it has a rather low specificity, since only absorption variations are considered, and the scattering is treated as an inevitable obstacle (John M. Steinke, A. P. Sheperd, "Role of Light Scattering in Spectrophotometric Measurements of Arteriovenous Oxygen Difference", IEEE Trans. BME-33, Aug. 8, 1986, p.729–734). Second, it has a rather low signal-to-noise ratio resulting from the low magnitude of the AC signal taken from natural blood kinetics.

When the first limitation has never been touched in practical devices (the scattering is considered to be too delicate and variable to deal with anywhere but in fundamental research), various methods have been suggested to improve the signal-to-noise ratio. Nearly all of them deal with artificially induced volumetric changes of either arterial or venous blood flow.

U.S. Pat. No. 4,883,055 discloses a method and device for artificially inducing blood pulse for use with a pulse oximeter. A cuff wrapped around a body member having an artery upstream from a testing site is adapted for applying a squeezing pulse to the body member, the squeezing pulse being synchronized with a normal blood pulse. Oxygen saturation in the arterial blood is determined based on spectrophotometric non-invasive measurements, which are effected according to the general approach of the above-mentioned AC-measurement technique.

U.S. Pat. No. 4,927,264 discloses a non-invasive apparatus and method for measuring blood constituents in venous blood. This technique utilizes the obstruction of a patient's venous blood stream, while the arterial blood stream is not obstructed. The venous blood stream is made time-variant by applying pressure with a peak value of the minimum blood pressure to a proximal portion from a measuring part.

U.S. Pat. No. 5,638,816 discloses a blood glucose monitoring system, which provides for inducing an active pulse in the blood volume of a patient according to a predictable cyclic pattern. The induction of an active pulse causes a cyclic change in the flow of arterial blood through a fleshy medium undergoing the test. By actively inducing a change of the blood volume, modulation of the volume of blood can be obtained to provide a greater signal-to-noise ratio. This enables constituents in blood to be detected at concentration levels below those previously detectable in a non-invasive system. Radiation, which passes through the fleshy medium, is sensed by a detector which generates a signal indicative of the intensity of the detected radiation. Signal processing is performed on the electrical signal to separate those optical characteristics of the electrical signal, which are associated with the optical characteristics of the blood.

To summarize, the absolute majority of existing devices in the field of non-invasive blood measurements utilizes the natural kinetics with all its limitations in signal-to-noise ratio.

SUMMARY OF THE INVENTION

The two main limitations of the most popular non-invasive methods are connected with the interpretation based on the omission of the scattering effects that results in the low specificity of measurements, and with the utilization of natural kinetics resulting in low signal-to-noise ratio. As a result, these methods are limited by the measurement of ingredients that have highly specific spectral behavior and are present in high concentrations (as $HbO_2$ does).

There is accordingly a need in the art to facilitate non-invasive optical measurements of various blood parameters, by providing a novel method enabling, on the one hand, the measurements with high signal-to-noise ratio, and, on the other hand, the determination of various blood parameters, also other than the oxygen saturation. These parameters may include the concentration of a substance in blood, such as glucose, hemoglobin, drugs or cholesterol, or other important blood parameters such as ESR, etc.

For blood parameters other than oxygen saturation, the determination is too problematic, because their absorption spectral behavior in red and near infrared regions is not as remarkable as for the oxygenized hemoglobin. Hence, the main limitations on the way of expanding the non-invasive techniques to the measurements different from pulse oximetry are associated with the limited selectivity of the absorption based method. In case of realistic accuracy of medical measurements for the absorption, which is not peculiar enough, the individuality of the patient becomes the main governing factor. To get rid of this limitation, scattering variations, which are more specific and sensitive than the absorption ones, have to be taken into account.

It is thus a major feature of the present invention to provide such a technique that takes into consideration both the light scattering and the light absorption in order to take into account the individual variability properly (contrary to the ideology of calibration of pulse oximeters, where light scattering is mostly ignored).

The basic idea of the invention is to combine the advantages of a high signal-to-noise ratio provided by a condition of artificial kinetics of optical characteristics (rather than natural kinetics of pulse oximetry) with high selectivity of light scattering based characteristics. The technique of the present invention is based on the convolution of spectral characteristics and artificial kinetics, and utilizes a particular kind of artificial kinetics favoring the high changes in light scattering.

The term "condition of artificial kinetics" used herein signifies a state of the patient's blood perfused fleshy medium at a measurement location, at which the parameters of the blood flow have changed in a predetermined manner, namely, at least one optical characteristic associated with the light response of blood (i.e., both absorption and scattering) has varied by a predetermined threshold value, and that the character of its change corresponds to the behavior of a time-dependent function (mostly non-periodic or, if periodic, having a period artificially imposed by the measurement system). The manner in which the changes of the blood flow parameters are obtained in order to realize the state of artificial kinetics is incorporated in both the basic physical model and digital signal processing (DSP) algorithms used in the processing of optical measurement results.

It is generally known that light scattering depends crucially on the shape of the scatterers and their optical characteristics (A. Ishimaru, "*Wave Propagation and Scattering in Random Media*", Vol. 1–2, Academic Press, New York, 1978). The scattering properties of blood depend on the size and shape of scatterers (aggregates). As for the absorption properties, they practically do not depend on the shape and size of scatterers, but depend almost entirely on the fraction of the components.

It has been found by the inventors that scattering assisted with erythrocyte aggregation demonstrates clearly a number of features associated with the geometry of scatterers. The difference in these features builds a theoretical basis in incorporating the light scattering characteristics in the non-invasive measurements and allowing for taking into account the individual characteristics. More specifically, it was found that light response characteristics (i.e., both absorption and scattering, but mostly scattering) of a blood perfused medium dramatically changes when a character of blood flow changes. Time changes of the light response (either monotonous or not, depending on the wavelength of incident radiation) at the condition of artificial kinetics are caused by the changes in the shape and average size of the scattering centers in the medium, i.e., red blood cells (RBC) aggregation (Rouleaux effect).

Preferably, the condition of artificial kinetics is established by creating a state of blood flow cessation at the measurement location caused by the application of over-systolic pressure at a location upstream of the measurement location with respect to the direction of normal blood flow (i.e., the so-called "occlusion-based technique"). Thus, the optical characteristics of the medium start to change in time, when creating the blood flow cessation, which induces the appearance of the condition of artificial kinetics of optical characteristics: the light response (transmission) of the medium grows (either monotonically or non-monotonically) as a result of occlusion, owing to the change of the shape and average size of the scattering centers in the medium, e.g., red blood cells (RBC) aggregation, etc. Hence, the light response of the medium undergoing the occlusion can be considered as the time dependence of scattering in a system with growing scatterers.

The most straightforward result of the above technique is in signal-to-noise ratio. Once the condition of artificial kinetics is created (e.g., the blood flow cessation state is established), the optical characteristics start to change dramatically, such that they differ from those of the fleshy medium with a normal blood flow by about 25 to 45%, and sometimes even by 60%. Hence, the accuracy (i.e., signal-to-noise ratio) of the optical measurements can be substantially improved by incorporating both the artificial kinetics of light response and the spectral behavior itself. The information is extracted from the time evolutions of light responses obtained with different wavelengths of incident light following the creation of the condition of artificial kinetics (e.g., the application of over-systolic occlusion). The light responses of the medium at these wavelengths essentially differ from each other. Even the monotonicity of time evolution of light response, say at 670 nm and at 960 nm, may be different.

Thus, the state of artificial kinetics in a blood perfused fleshy medium is connected with the dramatic change of Rouleau geometry. The time variations of light responses of the medium are thus created and measured, enabling to determine a required blood parameter as a function of at least two measurable parameters. At least one of these measurable parameters is derived from scattering spectral features of the medium highly sensitive to patient individuality, i.e., a so-called Roulaue Geometry Factor (RGF). At least one other measurable parameter is indicative of artificial kinetics of the optical characteristics of the patient's blood perfused fleshy medium, and is extracted from both the time evolution and the spectral behavior.

Thus, the present invention presents a technique for obtaining and analyzing the time changes of the spectral dependence of a light response of the patient's blood under the condition of artificial kinetics of optical characteristics, the changes resulting from the effect of scattering on particles of different size (erythrocyte aggregates). This technique utilizes the measurement of two groups of parameters indicative of respectively, scattering spectral features of the medium highly sensitive to patient individuality, and artificial kinetics of its optical characteristics. The two parameters are used for the determination of the desired blood parameter.

The construction of the first group parameter (RGF) is associated with the following. It was found that for one wavelength of the incident radiation, the time dependence of a light response (transmission signal) asymptotically falls down, and for another wavelength it grows. RGF essentially involves the different time evolutions of light responses at different wavelengths of incident radiation. RGF may serve as one of the key-parameters for attributing the measurement results for calibration purposes. In other words, RGF is such a parameter, whose different values can characterize different groups of patients, respectively.

Preferably, the first group parameter (RGF) is a certain "cut-off" wavelength $\lambda$ corresponding to the transmission value T staying nearly constant with time t, namely, the wavelength corresponding to the following condition: $\Delta T/\Delta t=0$ (or $\Delta(\log T)/\Delta t=0$). Alternatively, or additionally, the RGF may be a wavelength, $\lambda_{max}$, corresponding to a condition under which the ratio $\Delta(\log T)/\Delta t$ as the function of wavelength $\lambda$ has its maximal value. This enables to provide an additional calibration parameter, which is specific for a certain blood condition of a specific patient. Other peculiarities (well defined mathematically) of the ratio $\Delta(\log T)/\Delta t$ as the function of wavelength and/or time t enable to characterize the blood conditions of a specific patient, which can be utilized for calibration purposes.

As for the measurable parameter indicative of the artificial kinetics (second group parameter), it is a specific function of the values of a blood parameter to be determined, specific for each patient in the group of patients characterized, say, by the common or close value of the first group parameter, and can therefore be used for determining the desired blood parameter. This second group parameter may be one of the following: parametric slopes, time increments, phase shifts in case of modulated light beams and/or occlusions.

The typical example of the second group measurable parameter is determined as a relation between the time evolutions of light responses at different wavelengths, or characteristics' increments at the certain wavelength. This enables the explicit usage of the size of aggregates (i.e., the values that are unknown in experiments in vivo) to be eliminated.

A parametric slope is a slope of the line $T_{\lambda 2}(T_{\lambda 1})$ (or $\log T_{\lambda 2}(\log T_{\lambda 1})$), wherein $T_{\lambda 2}$ is the time dependence of the light response (transmission) of the medium irradiated with the wavelength $\lambda_2$, and $T_{\lambda 1}$ is the time dependence of the light response (transmission) of the medium irradiated with the wavelength $\lambda_1$. When a modulated light beam and/or modulated over-systolic pressure are applied, the phase shifts between input and output light signals may serve as the second group measurable parameters.

It should be noted that a parametric slope may actually also serve as RGF, and, consequently, may be used for calibration purposes as well. For example, the RGF may be presented in the form of a very certain combination of a few parametric slopes belonging to various time ranges of the artificial kinetics state.

There is thus provided according to the invention, a non-invasive method of optical measurements for determining at least one desired parameter of a patient's blood, the method comprising the steps of:

(a) providing reference data indicative of the at least one desired blood parameter as a function of at least two measurable parameters, wherein one of said at least two measurable parameters is derived from scattering spectral features of the medium, and said at least one other measurable parameter is indicative of artificial kinetics of the optical characteristics of the patient's blood perfused fleshy medium;

(b) creating a condition of the artificial kinetics and maintaining said condition for a certain time $t_c$;

(c) illuminating a measurement location on the medium with incident light beams of different wavelengths in a red-NIR range, detecting light responses T of the medium, and generating measured data indicative of time evolutions of the light responses, T(t), of the medium for said different wavelengths, respectively, during a time period t including said certain time $t_c$;

(d) analyzing the measured data for calculating values of said at least two measurable parameters;

(e) utilizing the calculated values and said reference data for determining a resulting value of said at least one desired blood parameter The time $t_c$ during which the condition of the artificial kinetics is maintained is such as to enable to follow resulting change in the optical characteristics of the medium with sufficient signal-to-noise ratio.

As indicated above, the condition of artificial kinetics may be created by applying an over-systolic pressure to the patient's blood perfused fleshy medium with a normal blood flow, so as to create a state of temporary blood flow cessation at the measurement location, and maintaining this state during a certain cessation time. The application of the over-systolic pressure may be constant during the cessation time (i.e., a single occlusion-release mode), or varying in a predetermined manner during the cessation time (i.e., a multiple occlusion-release mode). The cessation time is insufficient for irreversible changes in the fleshy medium, and may, generally, last from one second to one minute and more.

Additionally, periodical external pressure pulses of a controlled shape exceeding the systolic pressure in their maximum values, and then falling down to the normal pressure can be applied at the measurement location. This is actually the occlusion modulation procedure. This procedure may simplify drastically the processing of the measured data. Say, if the pressure pulses are strictly periodic in time, then the regular procedure of Fourier Transform may be applied to extract the parameter associated with artificial kinetics.

The reference data presents at least one desired blood parameter as a multiple-parameter function (i.e., the function of at least two measurable parameters). Thus, the reference data may be in the form of a plurality of calibration curves, such that each curve is in the form of the at least one measurable parameter of the second group as a function of values of the at least one desired blood parameter) and different calibration curves correspond to different values of the first group parameter (RGF). The reference data may be in the form of parametric surfaces, or tables.

The time interval (of the predetermined period of time) considered in the determination of the first group parameter (RGF) is the so-called "asymptotic time interval" that follows an initial time interval. The initial time interval is distinguished from the asymptotic time interval in that the transmission signals more strongly change with time during this interval, as compared to that of the asymptotic time interval. The time period considered in the determination of the second group parameter (e.g., parametric slope) may be the "initial time interval" (including the time during which the condition of artificial kinetics is maintained), or the "asymptotic time interval". The concrete procedure being used for measurements on a certain patient depends on the spectral position of the "far asymptotic", namely, the spectral position of a zero time derivative of the light response. This position is different for different wavelengths of incident light, and varies from patient to patient.

With regard to the different wavelengths of incident light, their number is selected so as to enable the determination of the RGF used for calibration purposes, and they include at least two wavelengths selected in accordance with the parameter to be determined. For example, if the hemoglobin concentration is to be determined, the two selected wavelengths are in those ranges, where the absorption properties of the hemoglobin and plasma are more sharply expressed, namely, 600–1000 nm and 1100–1400 nm. If the oxygen saturation is to be determined, the selected wavelengths lie in the range where the difference in the absorption of hemoglobin (Hb) and oxyhemoglobin (HbO2) are more sharply expressed, namely are in the ranges of 600–780 nm (HbO2 sensitive range) and 820–980 nm (Hb sensitive range). When dealing with the glucose concentration, the spectral ranges of 1500–1600 nm may be added to the above-mentioned range of 600–1300 nm for selecting the two wavelengths, respectively.

The analysis of the measured data may also comprise the determination of an additional measurable parameter indicative of increments of growth or decrements of decline of the light response by either exponential fits or windowed FT (or wavelet) analysis.

Having determined one of the second group measurable parameters (e.g., the parametric slope) for a specific patient, a corresponding reference data portion (e.g., calibration curve), is used for determining the desired blood parameter for the specific patient (i.e., characterized by a specific value of the first group parameter). The reference data is prepared by applying measurements of the present invention (steps (b) to (d)) and the conventional ones to different patients, and determining the first and second group parameters, and the desired blood parameter.

For the determination of oxygen saturation, generally, reference data may be prepared by applying measurements of the present invention to a specific patient, at the multiple occlusion-release mode at the blood flow cessation state in a breath hold experiment.

The method of the present invention involves both the active influence on the parameters of blood flow in the medium resulting in the artificial kinetics of the optical characteristics of the medium, and the spectrometric measurements of various time depending features. The method establishes these time varying features, their time positions, and dominating trends in between for a number of wavelengths within the spectral range of a sensor. All these factors taken together build the basic information for blood parameter measurement. Then, based on this information, appropriate processing is applied for transforming the time trends to at least one desired blood parameter (the concentration of glucose and/or hematocrit, cholesterol, erthrocyte sedimentation rate (ESR), etc.).

The method of the present invention is simple and ensures a relatively high signal-to-noise ratio because of the usage of artificial kinetics, as compared to the methods utilizing measurements based on natural kinetics (i.e., synchronized with the blood pulse). This is owing to the fact that the present invention enables the parameters of the unchanged blood sample to be determined by using two or more readings of significantly distinct amplitudes. This method also allows for extracting substantially higher amount of information, as compared to conventional methods (either invasive or non-invasive), because spectral behavior of artificial kinetics accompanying the over-systolic occlusion depends strongly on a number of blood parameters: glucose, ESR, hematocrit, etc.

Such an approach has not ever been used or suggested in the prior art. This is actually an advantageous combination of the principles of artificial kinetics offering a high signal to noise ratio, and scattering assisted spectral peculiarities offering high sensitivity to patient's individual features.

As indicated above, the optical characteristics of a blood perfused fleshy medium at the state of blood flow cessation differ from those of the fleshy medium with normal blood flow by about 25 to 45%, and sometimes even by 60%. Conventional methods of pulse oximetry make use of fluctuations of light transmitting characteristics in the range of about 2%.

Since the novel method enables to obtain a spectrum of readings differing from each other by up to 60%, more than two sessions may be chosen for effecting the measurements and for further statistical processing of the obtained results. Additionally, it has been found that the method effects an extremely high correlation between values of the concentration obtained from the measurements. Hence, determining of concentration may comprise comparison and cross-validation of the results obtained from two or more measurements. The comparison and cross-validation may include the calculation of the average and a statistical procedure of standard deviation values. Information about a statistical error in a specific measurement may be of a great importance for a physician or a customer.

The method is preferably intended for measuring the concentration of chemical or biological substances, which are present in the blood, regardless of the character of its flow. It should, however, be noted that the method can also be used for determining blood oxygen saturation and/or other parameters that depend on the existence of a normal blood pulse, provided additional conditions and approximations are taken into consideration.

The inventive method can be used both for independent measurements and for calibration of other non-invasive methods intended for obtaining similar data and based on measurements synchronized with the blood pulse, for example, methods for the continuous monitoring of blood parameters at departments of intensive care in hospitals.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 7A illustrates three calibration curves corresponding to three different values of a cut-off wavelength (RGF), respectively, used for the determination of hemoglobin concentration; FIG. 7B illustrates three calibration curves corresponding respectively to the three different values of the cut-off wavelength used for the determination of oxygen saturation;

FIGS. 8A and 8B illustrate the determination of the oxygen saturation parameter by applying the two kinds of measurements for a specific patient in a breath holding experiment using a multiple-occlusion mode, wherein FIG. 8A shows measured data in the multiple-occlusion mode, and FIG. 8B shows a calibration curve plotted using the data from FIG. 8A;

FIGS. 9A and 9B illustrate the principles of a "Megaslope" concept, the "Megaslope" constituting a measurable parameter that can be used for determining a desired blood parameter, wherein FIG. 9A shows a graph determined from the measured data of FIG. 3, and FIG. 9B shows a calibration curve in the form of the MegaSlope as the function of hemoglobin concentration;

DETAILED DESCRIPTION OF A PREFERRED EMBODIMENT

A method according to the present invention consists of creating the condition of artificial kinetics of the optical characteristics of a patient's blood perfused fleshy medium, and applying optical measurements thereto. The condition of artificial kinetics is created at the state of blood flow cessation. To this end, over-systolic pressure is applied to the patient's blood perfused fleshy medium, e.g., his finger, so as to create the state of blood flow cessation and maintained during a certain cessation time. The measurement location (located downstream of the location under pressure with respect to the direction of blood flow) is irradiated with different wavelengths in the red or NIR range. Light responses (transmission or reflection) as the functions of time are detected during a predetermined time period, including the cessation time.

Figure 1:
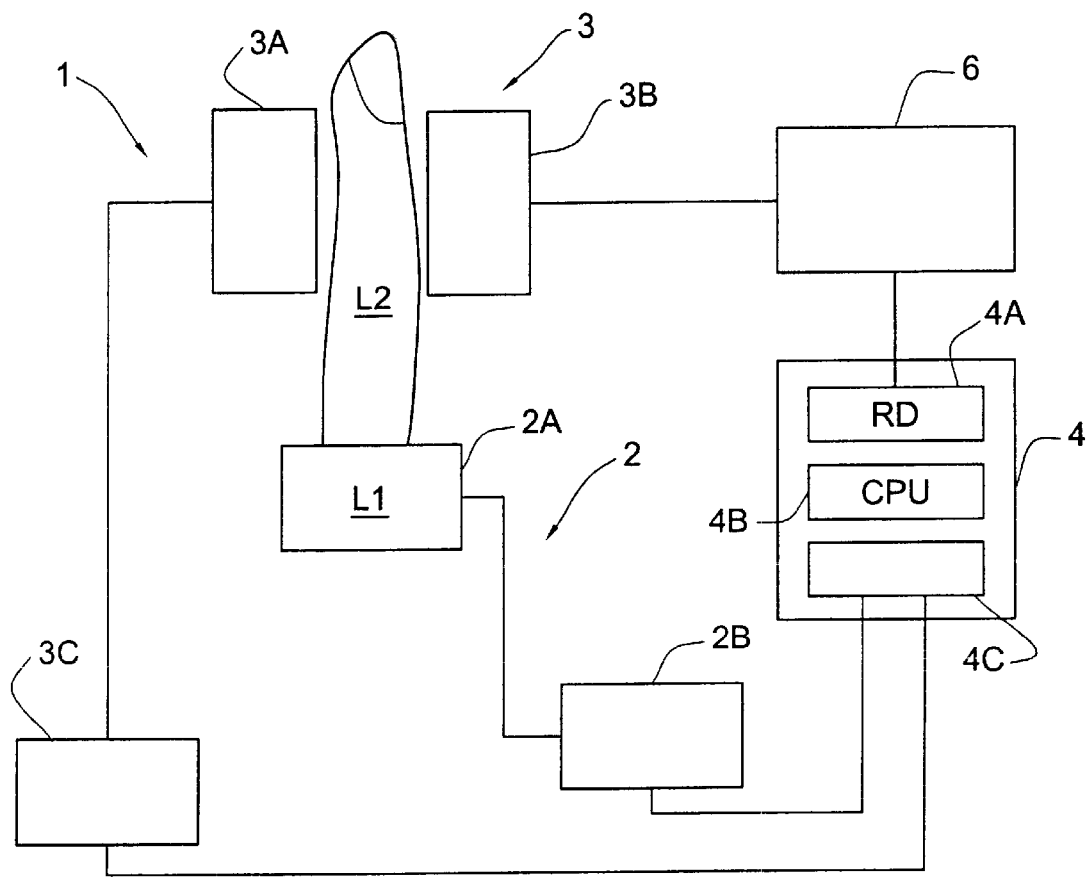
FIG. 1 is a schematic block diagram of the main components of a measuring apparatus according to the invention.

FIG. 1 illustrates a block diagram of a measuring apparatus 1 for carrying out the method of the present invention. The apparatus 1 includes such main constructional parts as a pressurizing assembly 2 (occluder); a measuring unit 3, and a control unit 4.

The pressurizing assembly 2 is composed of an occlusion cuff 2A, which may be of any known suitable type for attaching to the patient's finger at a location $L_1$, and a driver 2B actuated by the control unit 4 for operating the squeezing of the cuff 2A. The measuring unit 3 comprises an illumination assembly 3A and a light collection/detection assembly 3B. The illumination assembly 3A includes a plurality of light sources (e.g., LEDs), which are not specifically shown, associated with a suitable drive mechanism 3C operated by the control unit 4. Alternatively, a single broad band illuminator can be used. The light sources generate incident radiation propagating through the medium at a measurement location $L_2$.

The light collection/detection assembly 3B includes one or more frequency selective detectors, e.g., spectrophotometer or photodiodes with frequency selective filters, typically equipped with an amplifying means that are not specifically shown. Generally, the detection assembly 3B is accommodated so as to detect light response of the medium at the measurement location, namely, light transmitted through the medium (or light reflected therefrom, as the case may be), and to generate data representative thereof (constituting measured data). In the present example, light transmitted through the medium is detected (constituting the light response of the medium). The output circuit of the assembly 3B is coupled to the control unit 4 through a suitable electronic block, typically including an analog to digital (A/D) converter (not shown).

The control unit 4 is a computer device having such known utilities as a memory 4A for storing reference data (RD), a processor (CPU) 4B, a synchronizer 4C, and a monitor 6. The processor is preprogrammed by a suitable software model capable of analyzing the received output of the detection assembly 3B (measured data) and determining one or more desired conditions of the patient's blood, as will be described more specifically further below. As shown, the control unit 4 is interconnected between the measuring unit 3 and the pressurizing assembly 2 for operating the drivers 3C and 2B, and is coupled to the output of the detection assembly 3B to be responsive to the measured data.

It should be noted that the cuff 3A may be accommodated on the patient's wrist or palm, and the illumination and detection assemblies may be located on the patient's finger. Generally speaking, the first and second locations $L_1$ and $L_2$ to which the pressure and measurements are applied, respectively, are aligned along the direction of the normal blood flow.

Figure 2:
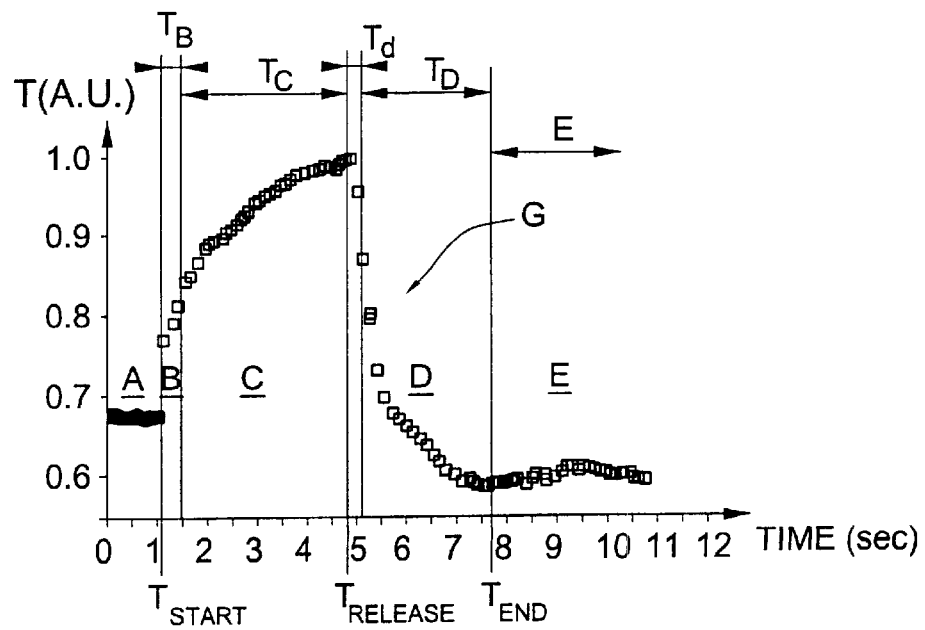
FIG. 2 illustrates a graph showing fluctuations of light transmitting characteristics of blood, which is experimentally obtained by applying the system of FIG. 1 to a fleshy medium.

FIG. 2 illustrates a graph G presenting experimental results obtained by applying the apparatuses 1 to the patient's blood perfused fleshy medium. The graph G shows how the light-transmitting characteristic of blood changes under the application of the over-systolic pressure. The transmitting characteristic are shown here as the so-called "relative Transmission", i.e., in Transmission Arbitrary Units or T(A.U.).

The application of pressure starts at a moment $t_{start}$, and is maintained for a period of time such as not to cause irreversible changes in the fleshy medium (e.g., 4 seconds). The pressure is released at the moment $t_{release}$. Measurements of the Relative Transmission are performed continuously, starting prior to the application of the over-systolic pressure. Different states of the blood flow, designated A, B, C, D and E, are observed.

State A is a state of normal blood flow before the over-systolic pressure is applied. As shown, this state is characterized by a standard fluctuating value of the relative light transmission of blood. State B starts at the moment $t_{start}$ (when the pressure is initially applied) and exists during a short period of time $t_B$ (about 0.5 sec) following the actual start of occlusion. Measurements taken during this time period should be disregarded, due to the unavoidable influence of motional and/or other artifacts causing non-monotonic fluctuations of the light transmission. State C is a state of the temporary cessation of blood flow, which lasts within a cessation time $t_C$ between a moment determined as $(t_{start}+t_B)$ and the moment $t_{release}$. During this cessation time, $t_C$, the ascending curve (or descending curve depending on the incident wavelength) of relative light transmission of blood is observed. It reaches its maximum, and may last for about 2–5.5 sec (generally, from one second to several minutes).

It is appreciated that when over-systolic pressure is applied to any proximal part of the body, there is still sufficient space for the redistribution of blood between the exact area of the measurement (i.e. the location of the detector) and the adjacent areas in close proximity to the detector. For example, if the detector is located on a fingertip and over-systolic pressure is applied on the palm, there is enough space between the fingertip and the margin of the applied pressure to "squeeze" the blood from one location to another.

State D is a transitional state of blood flow, which takes place after releasing the over-systolic pressure. This state starts with a slight delay $t_d$ (approximately 0.5 sec), i.e. at the moment determined as $(t_{release}+t_d)$. During the time period $t_D$ of the duration of state D, the relative transmission of blood monotonously descends until it reaches values characteristic of the normal blood flow. Such a moment is marked as $t_{end}$ in the drawing. The end of state D, and the beginning of state E, is detected when the changes of the light transmission become periodic and minimal (about 2%). State E is a state of normal blood flow, which is similar to state A.

The optical measurements are applied during a time period including the cessation time with at least two different wavelengths of incident light, and corresponding transmission signals (light responses) are measured as the functions of time.

Figure 3:
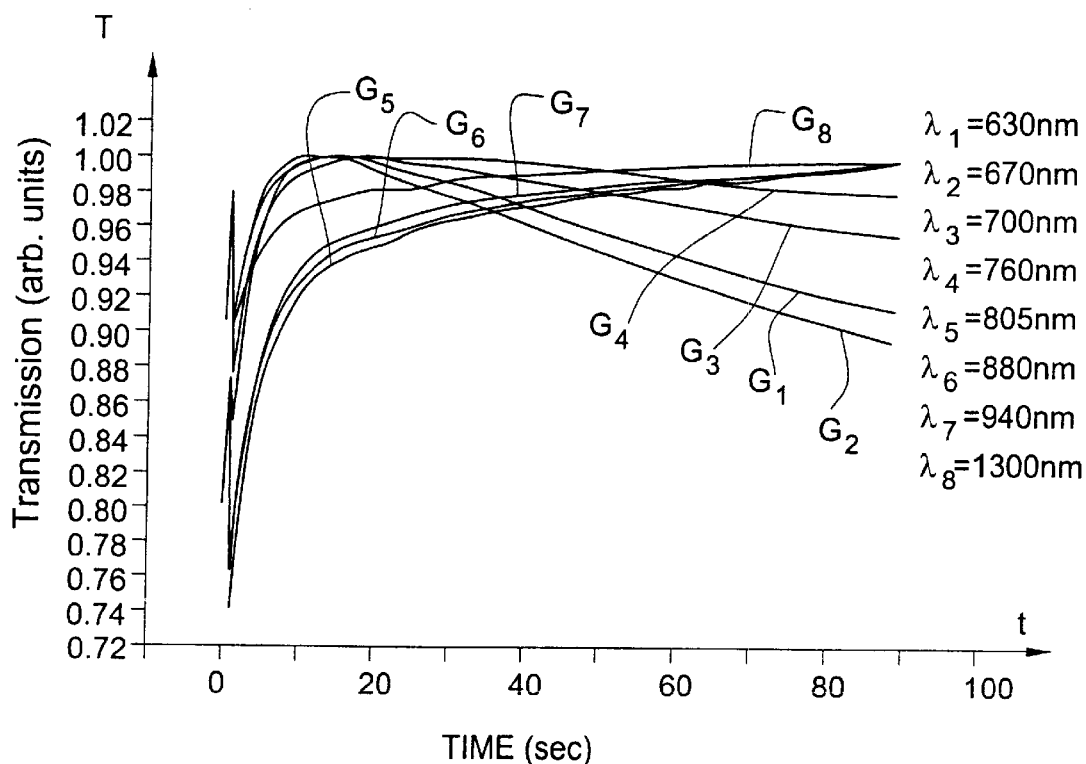
FIG. 3 illustrates graphs showing the measured time variations of the s transmission signals, corresponding to different wavelengths, all measured by the apparatus of FIG. 1.

FIG. 3 illustrates eight graphs $G_1$–$G_8$ showing the measured time variations of the transmission signals as functions of time, $T_1(t)$–$T_8(t)$, corresponding to different wavelengths of incident light, namely, $\lambda_1$=630 nm, $\lambda_2$=670 nm, $\lambda_3$=700 nm; $\lambda_4$=760 nm; $\lambda_5$=805 nm $\lambda_6$=880 nm; $\lambda_7$=940 nm, and $\lambda_8$=1300 nm, respectively, obtained with the apparatus 1 applied to a specific patient. As shown, the transmission always grows during a certain initial time interval, which is different for different wavelengths of incident radiation, and then, in an asymptotic time interval, it monotonously grows or falls, depending on the wavelength of the incident light.

Since for one wavelength the transmission signal grows with time in the asymptotic time interval and for the other wavelength it falls, there exists such a wavelength (cut-off wavelength) of incident radiation, which causes nearly no time changes in the transmission signal in an asymptotic region, i.e., in a time range close to moment $t_{release}$. The transmission signal corresponding to the cut-off wavelength of incident radiation becomes therefore slightly dependent on time.

Figure 4:
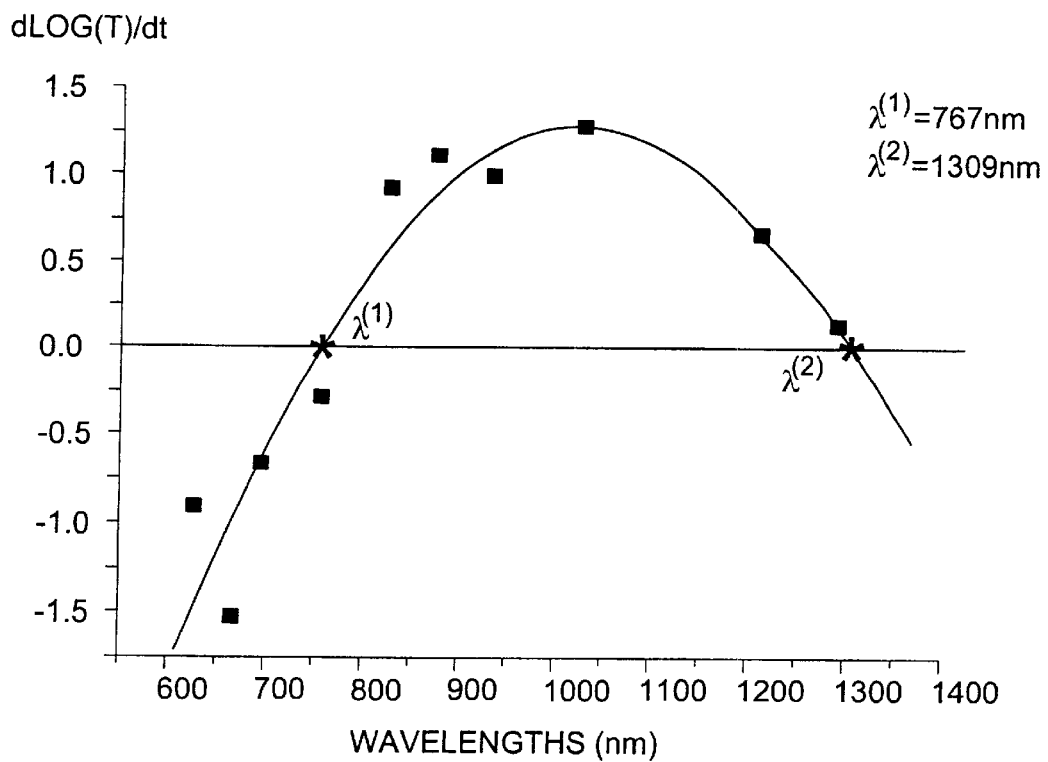
FIG. 4 illustrates how data from the graphs of FIG. 3 can be utilized for the determination of one of the measurable parameters, presenting the RGF to be used for calibration purposes.

FIG. 4 shows a graph in the form of a ratio $\Delta(\log T)/\Delta t$ as the function of wavelength $\lambda$ obtained from the graphs in FIG. 3, wherein $\Delta t$ lies substantially within the asymptotic time interval, during which the transmission signals change with time slower t in the initial time interval The points $\lambda^{(1)}$ and $\lambda^{(2)}$ are the cut-off wavelengths of incident light corresponding to a certain time stable transmission ($\Delta(\log T)/\Delta t=$ 0) for a specific patient or a group of patients. In the present example, $\lambda^{(1)}$=767 nm and $\lambda^{(2)}$=1309 nm. These parameters $\lambda_1$ and $\lambda_2$ are associated with the peculiarity of the patient, and is the example of RGF.

Another measurable parameter that can be obtained from the measured data (FIG. 3) is a parametric slope PS. To determine a parametric slope PS, the time variations of the light responses corresponding to two different wavelengths of incident light are utilized (FIG. 3), and the light response for one wavelength is plotted as the function of the light response for the other wavelength, preferably in logarithmic coordinates. To this end, the initial time intervals, as well as the asymptotic time intervals can be considered. The wavelengths are selected in accordance with the blood parameter to be determined.

Figure 5:
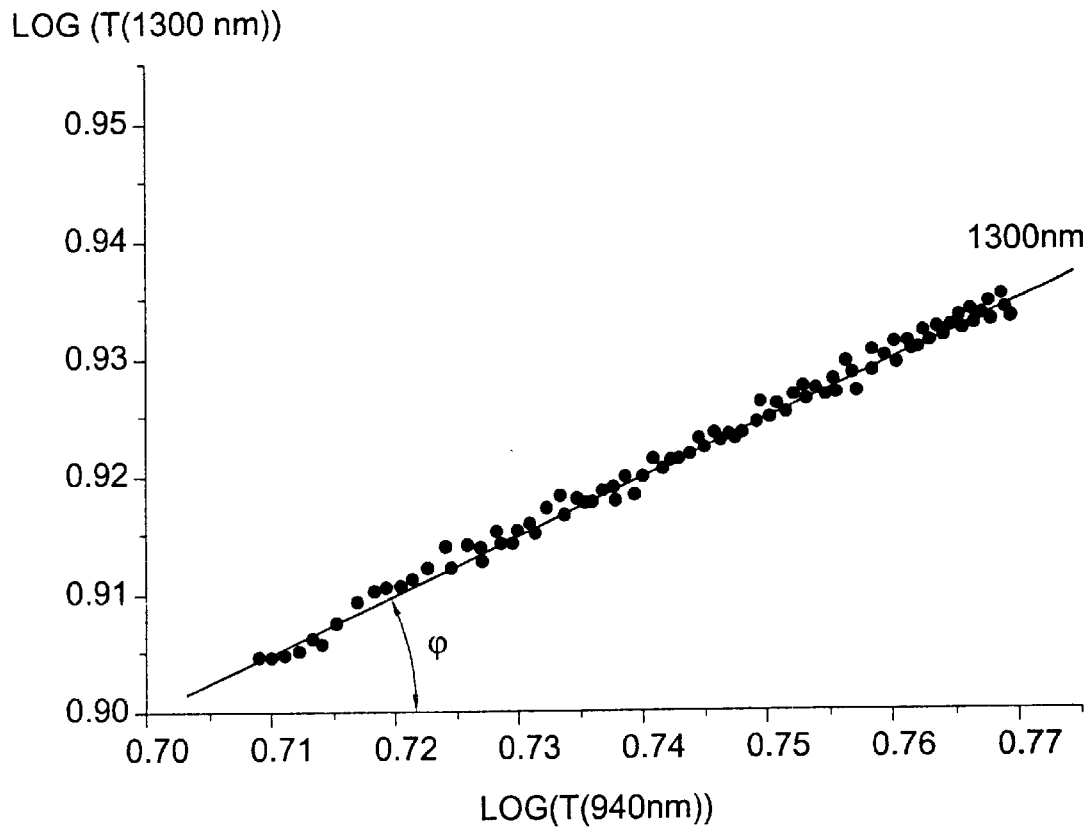
FIG. 5 illustrates how data from the graphs of FIG. 3 can be utilized for the determination of another the measurable parameter, namely, a parametric slope, to be used for the determination of the concentration of hemoglobin.

The example of the determination of the parametric slope aimed at determining the hemoglobin concentration is shown in FIG. 5. The parametric slope PS is determined as the value of $tg(\phi)$ of a line plotted as the function of the transmission logarithm at the wavelength $\lambda_8$, i.e., $Log(T_8)$, versus the transmission logarithm at the wavelength $\lambda_7$, i.e., $Log(T_7)$. In tis example, the wavelengths $\lambda_7$=940 nm and $\lambda_8$=1300 nm are selected for the determination of the hemoglobin concentration. This graph is obtained by the linear regression algorithm. The parametric slope PS is equal to 0.6.

Another important blood parameter that can be determined with the invented method is the oxygen saturation in the patient's blood. Oxygen saturation is defined as the ratio of the content of oxyhemoglobin ($HbO_2$) to the total amount of hemoglobin (Hb) in the blood volume unit. The classic pulse oximetry method allows for determining the oxygen saturation. This method utilizes the so-called "natural pulsatile" component of a light transmission signal. This pure natural pulse-related signal component of a detected signal, determined by an appropriate signal processing technique, is commonly called the "AC component" of the detected signal, whereas the entire transmission signal by itself is called the "DC component" of the detected signal. The transmission measurements in the pulse oximetry are carried out simultaneously at two different wavelengths, for example $\lambda_4$=760 nm and $\lambda_7$=940 nm, where the significant difference in the light absorption of oxyhemoglobin and hemoglobin exists between the two chosen wavelengths. Two pairs of AC and DC components are obtained. Generally, the ratio R, defined as $(AC/DC)_{\lambda 4}/(AC/DC)_{\lambda 7}$, is the value of oxygen saturation.

Figure 6:
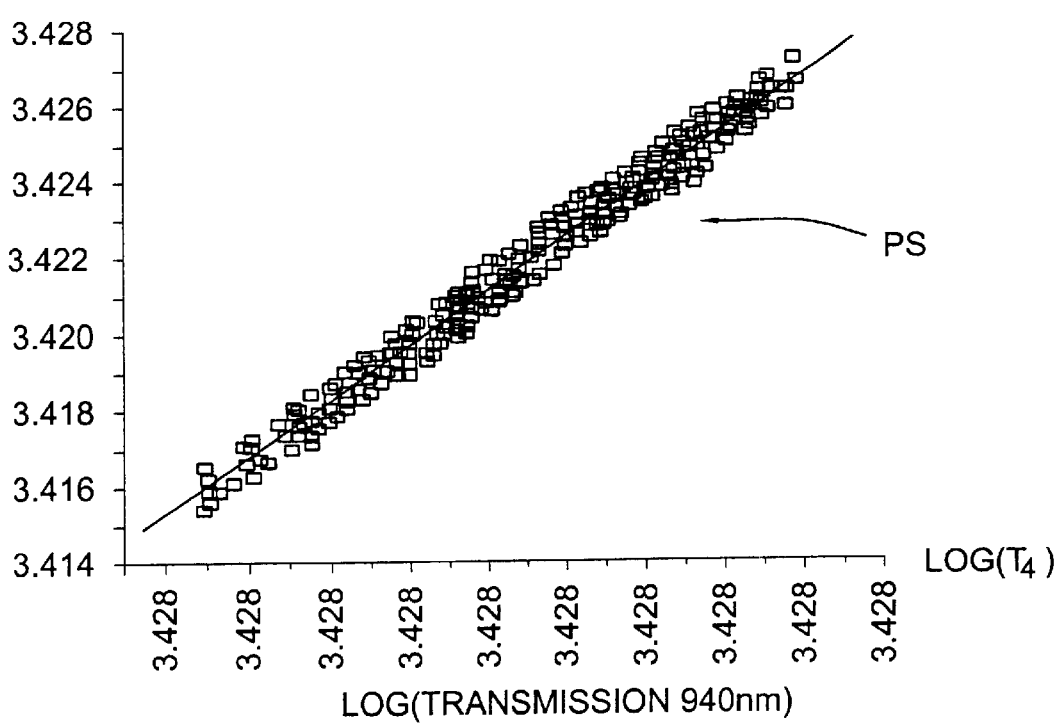
FIG. 6 illustrates how data from the graphs of FIG. 3 can be utilized for the determination of a parametric slope to be used for the determination of the oxygen saturation.

The "parametric slope" concept provides the same results as with the pulse oximetry technique. FIG. 6 illustrates a graph $(\log T_4)_{\lambda 4}$ vs. $(\log T_7)_{\lambda 7}$, plotted using the corresponding data of FIG. 3. A parametric slope is determined as $tg(\phi)$, and is equal to 0.69.

It should be noted, although not specifically shown, that by appropriately selecting the measured data (FIG. 3), parametric slope values suitable for the determination of over parameters (e.g., the concentration of glucose) can be determined.

Figure 7A:
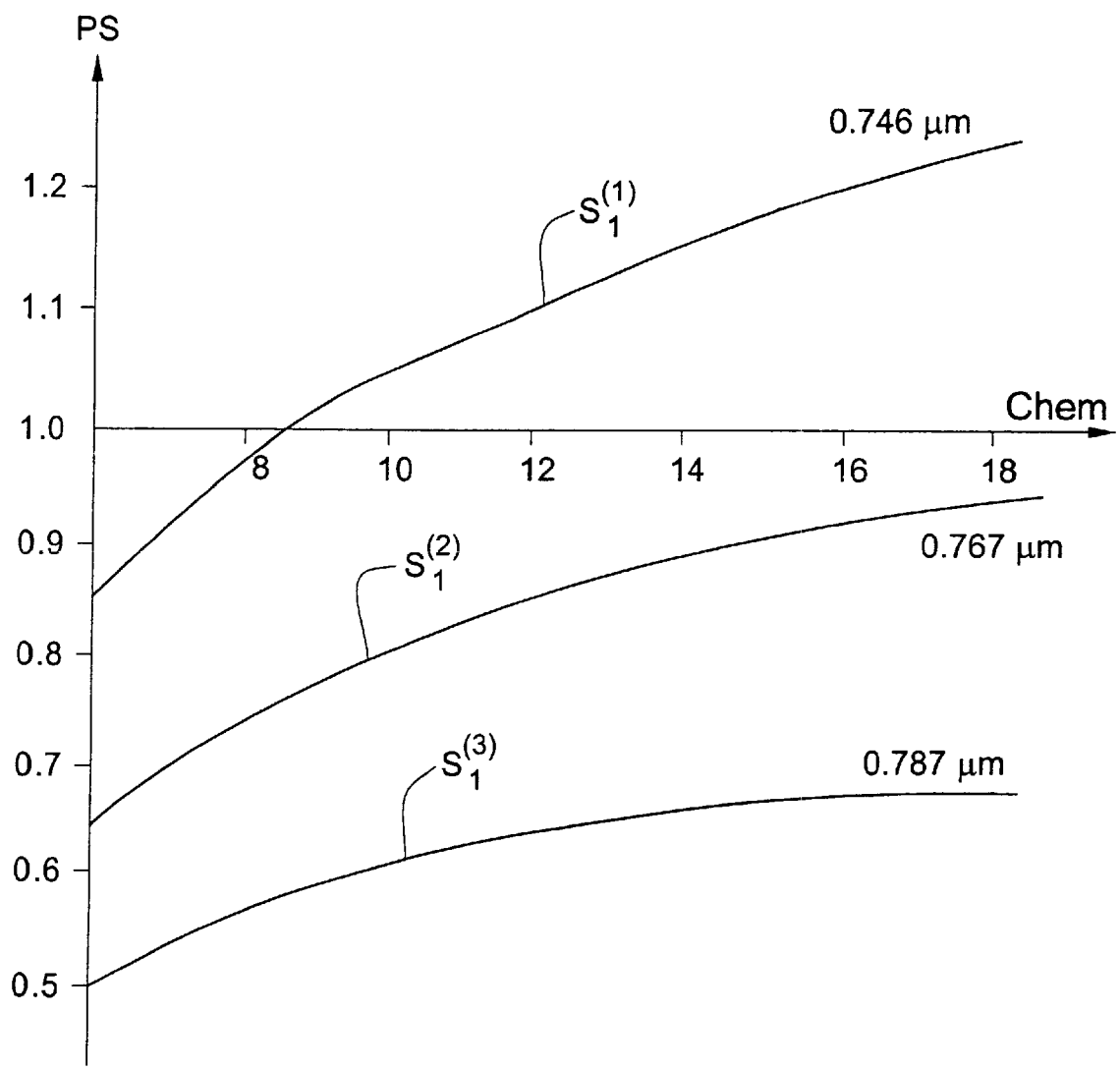
FIGS. 7A and 7B illustrate reference data in the form of calibration curves suitable to be used in the method of the present invention.
Figure 7B:
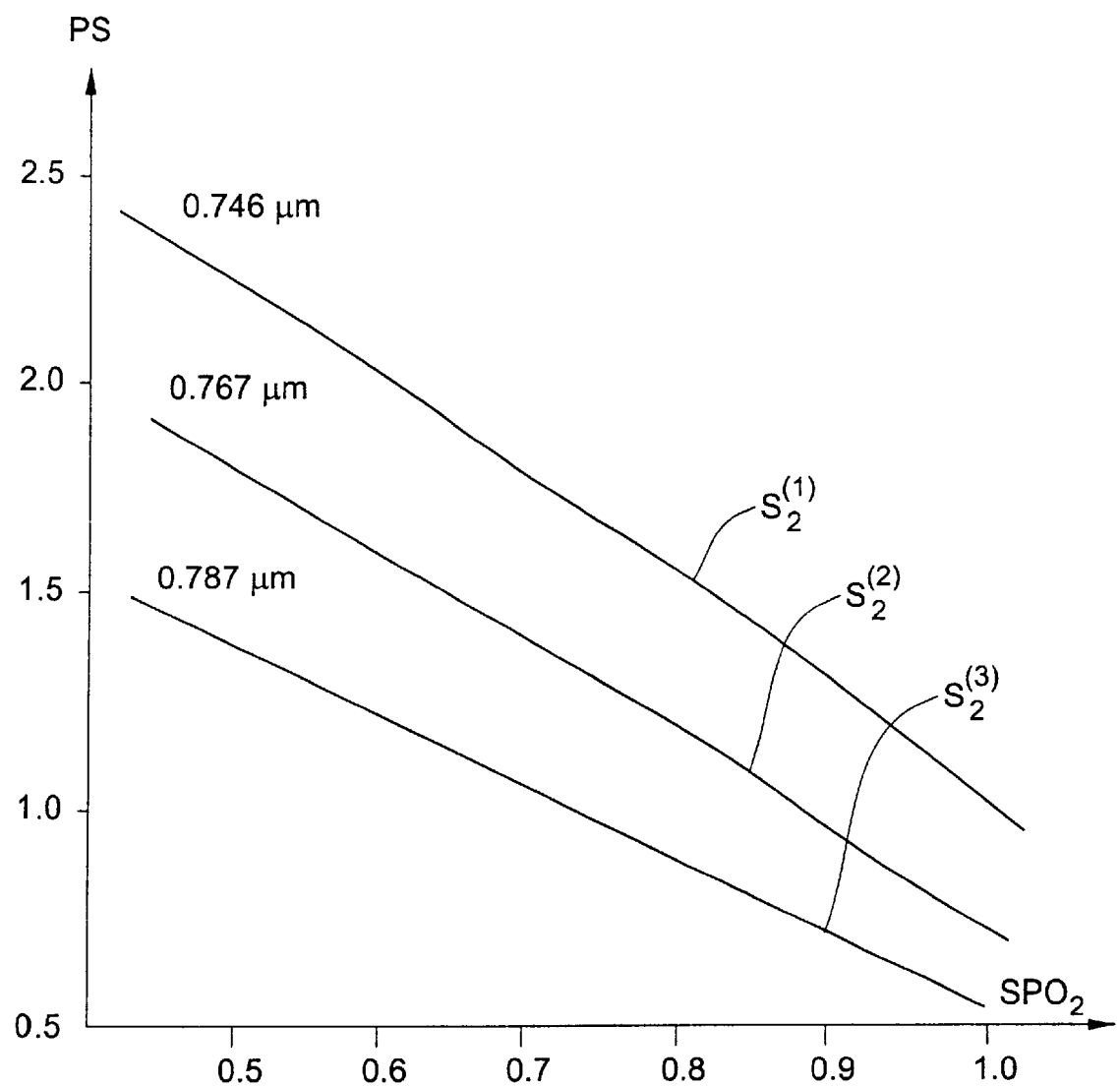

Reference is now made to FIGS. 7A and 7B illustrating reference data in the form of two sets of calibration curves, respectively, each set including three calibration curves $S_1^{(1)}$–$S_1^{(3)}$ and $S_2^{(1)}$–$S_2^{(3)}$ used for the determination of different blood parameter—hemoglobin concentration and oxygen saturation. The different calibration curves in each set correspond to different values of a cut-off wavelength (RGF), respectively.

More specifically, FIG. 7A shows curves $S_1^{(1)}$, $S_1^{(2)}$ and $S_1^{(3)}$ presenting the parametric slope PS (measurable parameter) as different functions of hemoglobin concentration $C_{hem}$ for different values of the cut-off wavelengths, respectively, namely, $\lambda^{(1)}$=746 nm, $\lambda^{(2)}$=767 nm and $\lambda^{(3)}$=787 nm. These three curves relate to three different groups of patients characterized by different values of the cut-off wavelength. Curves $S_2^{(1)}$, $S_2^{(2)}$ and $S_2^{(3)}$ (FIG. 7B) show the values of parametric slope PS as three different functions of oxygen saturation for the cut-off wavelengths $\lambda^{(1)}$=746 nm, $\lambda^{(2)}$=767 nm and $\lambda^{(3)}$=787 nm, respectively.

It is thus evident, that in this specific example of FIG. 4 ($\lambda_1$=767 nm and $\lambda_2$=1309 nm), the calibration curves $S_1^{(2)}$ and $S_2^{(2)}$ will be used for the determination of the patient's blood parameters, i.e., the hemoglobin concentration and the oxygen saturation.

Thus, by determining (from the measured data of FIG. 3) the values of a cut-off wavelength (FIG. 4) and of a parametric slope (FIGS. 5 and 6) for the specific patient to whom the measurements are applied, and utilizing corresponding calibration curves (FIGS. 7A and 7B), the desired blood parameters can be determined. In this specific example, the determined values of the desired parameters are: $C_{hem}=6$ and the oxygen saturation $SPO_2$ is equal to 0.91.

As indicated above, a calibration curve to be used for determining the oxygen saturation for a specific patient may, in general, be constructed by applying measurements to various patients. Alternatively, or additionally, in the case of oxygen saturation determination, the calibration curve can be plotted when applying the two kinds of measurements for a single patient in a breath hold experiment using a multiple-occlusion mode. This is illustrated in FIGS. 8a and 8b.

Figure 8A:
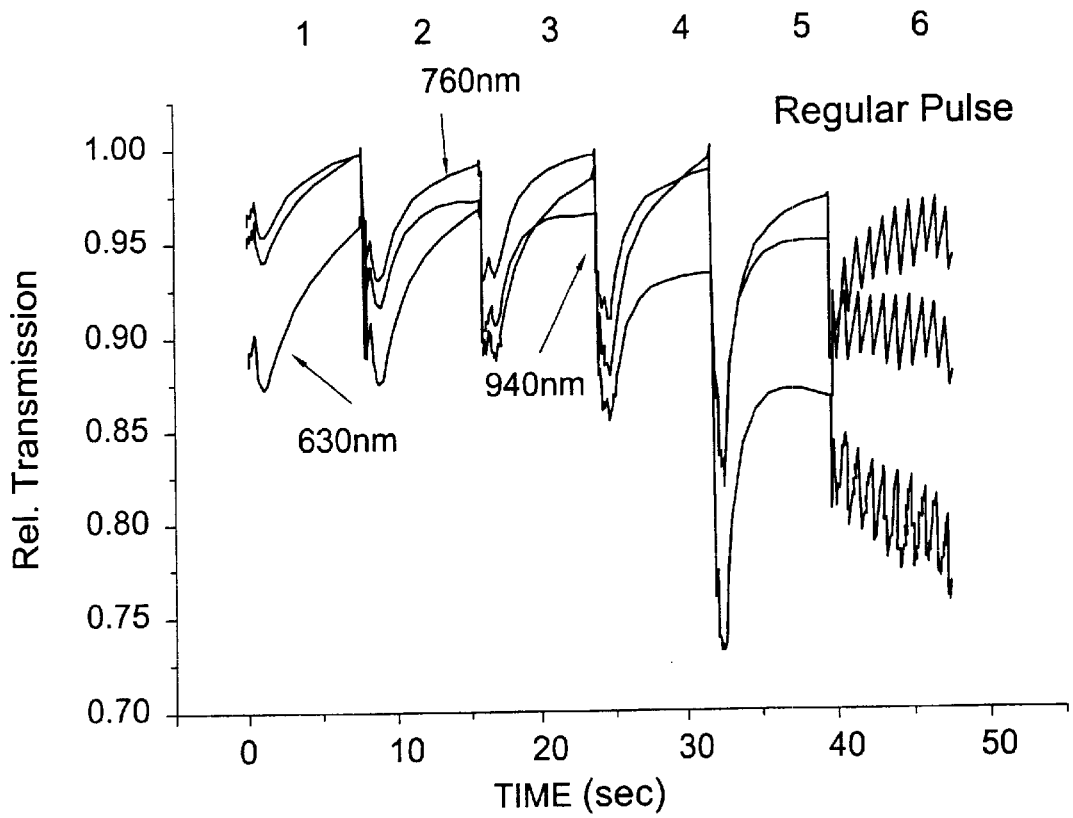
Figure 8B:
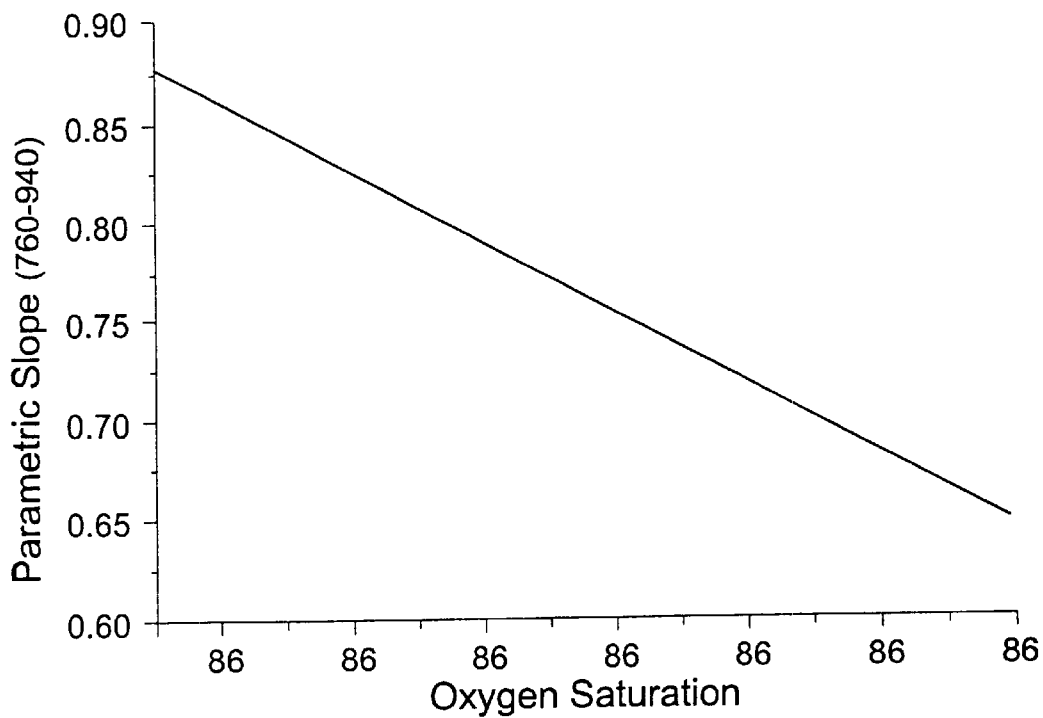

FIG. 8a shows the measured data in the multiple-occlusion mode in the form of the transmission functions $T_1(t)$, $T_2(t)$ and $T_3(t)$ corresponding, respectively, to the wavelengths $\lambda_1=630$ nm, $\lambda_2=760$ nm and $\lambda_3=940$ nm. As shown, several occlusions were performed during the state of the patient's breath hold, and the corresponding parametric slope values were determined during the time interval of the saturation decrease. Concurrently, conventional measurements are applied to the same patient, for example to his other finger, for determining the changes in the oxygen saturation. FIG. 8b shows the so-obtained calibration curve in the form of the parametric slope PS as the function of the oxygen saturation $SPO_2$.

Figure 9A:
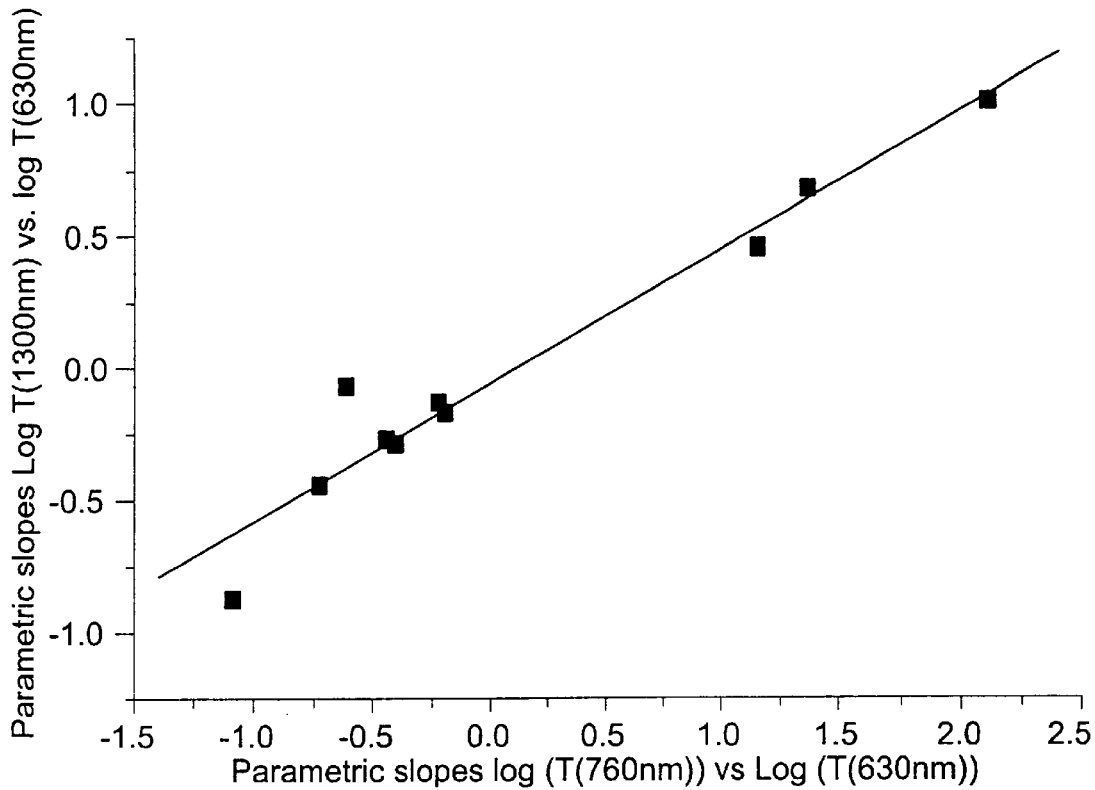
Figure 9B:
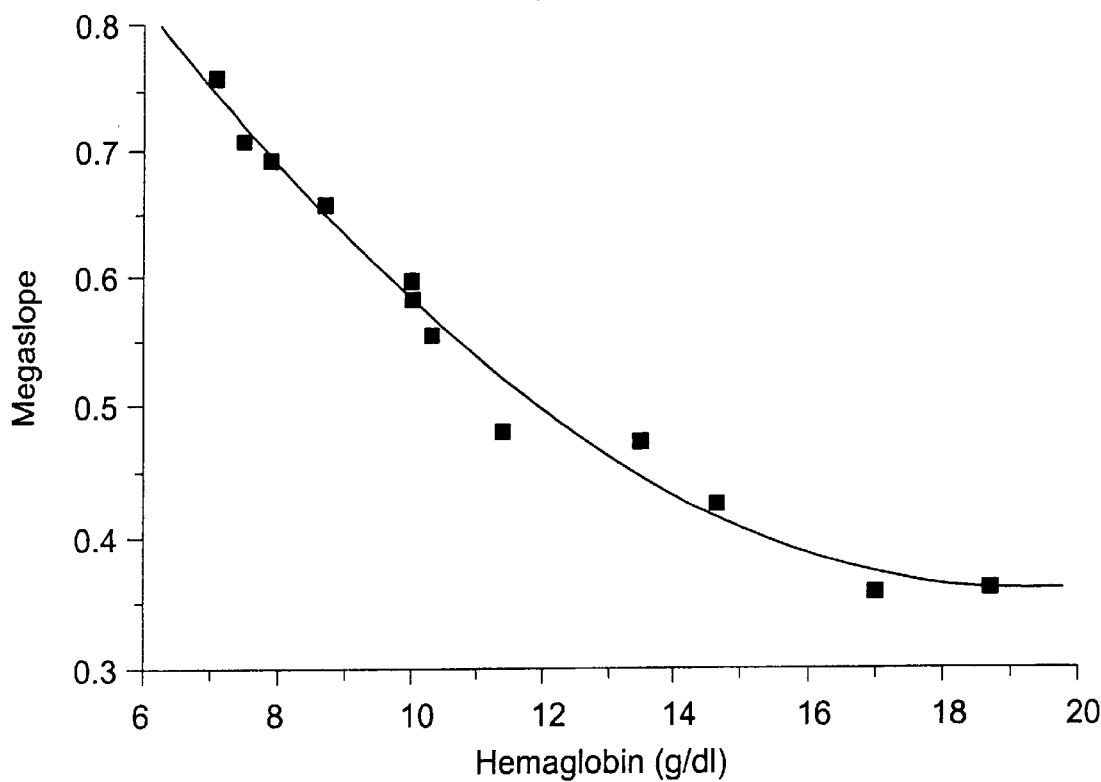

FIGS. 9a and 9b illustrate another example of one of the measurable parameters, a so-called "MegaSlope" (MS), which can be used for determining a desired blood parameter. FIG. 9a shows a graph determined from the measured data shown in FIG. 3, using the light responses corresponding to wavelengths $\lambda_1=630$ nm, $\lambda_4=760$ nm and $\lambda_8=1300$ nm. To this end, the entire time period in FIG. 3 is divided into a plurality of time intervals $\Delta t$—ten such intervals in the present example. For each time interval $\Delta t$, a pair of parametric slope values is obtained from the following: $(\log T)_{\lambda 8}$ vs. $(\log T)_{\lambda 1}$ and $(\log T)_{\lambda 4}$ vs. $(\log T)_{\lambda 1}$. In other words, each point in the graph shown in FIG. 9a corresponds to a pair of parametric slopes calculated for a pair of wavelengths $\lambda_8-\lambda_1$ and $\lambda_4-\lambda_1$, respectively, each for a corresponding one of the time intervals $\Delta t$. Each such parametric slope is determined in the above-described manner. The MegaSlope is determined as $tg(\phi)$. A calibration curve shown in FIG. 9b presents the MegaSlope as the function of hemoglobin concentration, i.e., MS(H).

Figure 10:
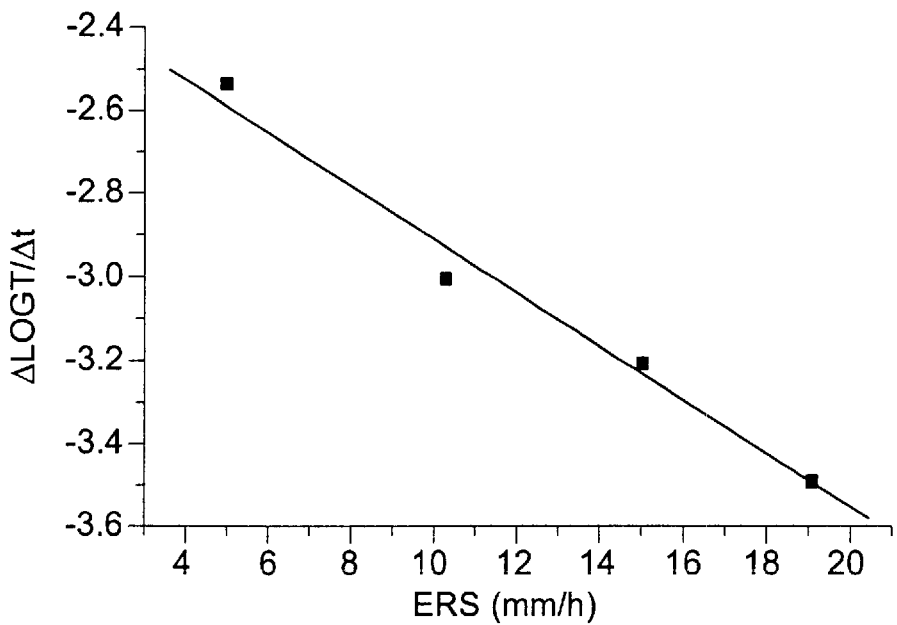
FIG. 10 illustrates the correlation between the values of Erythrocyte Aggregation Rate (EAR) obtained by the present invention and the values of Erythrocyte Sedimentation Rate (ESR) measured in the conventional in vitro manner.

One more important feature of the present invention consists of determining the Erythrocyte Aggregation Rate (EAR) for a specific patient. Assuming that the only process that takes place at the state of the blood flow cessation is the erythrocytes' aggregation, the EAR can be simply determined as the rate of the time changes of light response signal, i.e., $\Delta T/\Delta t$ (or $\Delta \log T/\Delta t$). To this end, the transmission as the function of time is measured with one wavelength of incident radiation. For more precise measurements, two such transmission signals as functions of time are measured with two different wavelengths of incident radiation. As for the time interval $\Delta t$, it may be either initial time interval or asymptotic time interval. The EAR parameter can be used for the determination of such an important parameter as Erythrocyte Sedimentation Rate (ESR). This is illustrated in FIG. 10, showing the correlation between the values of EAR measured as described above ($\Delta \log T/\Delta t$) and the values of ESR measured in the conventional in vitro manner.

Figure 11:
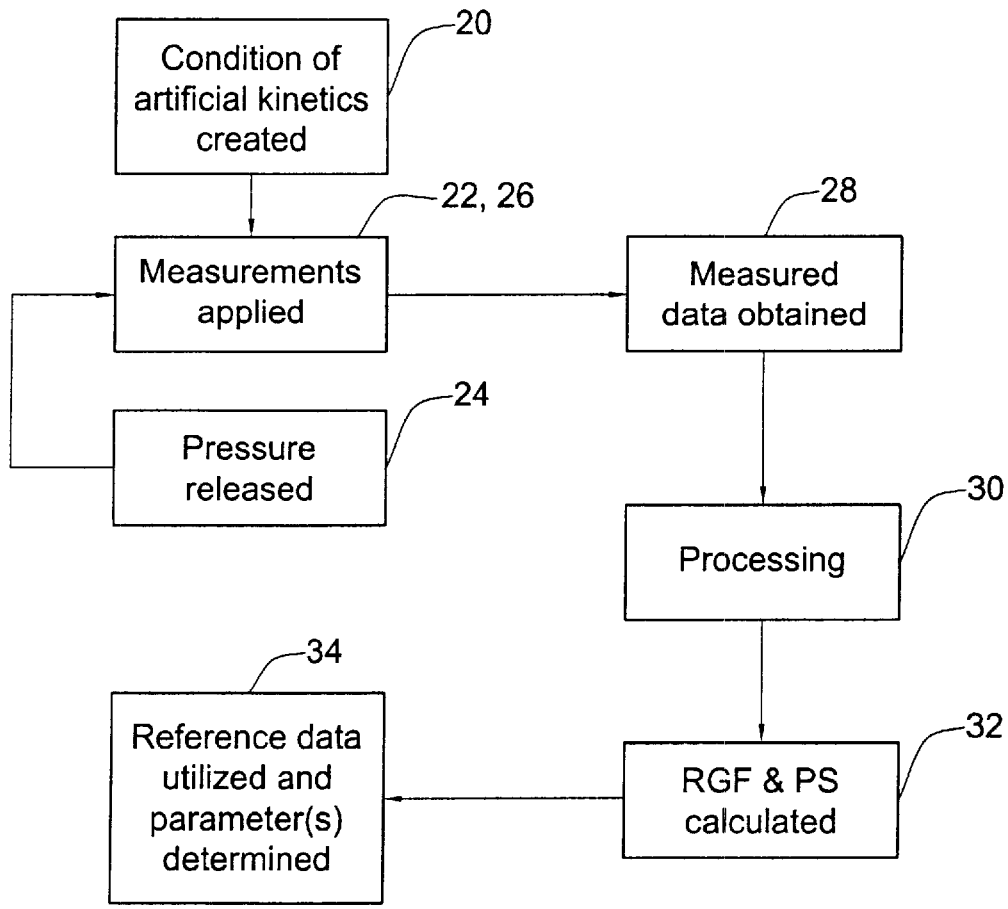
FIG. 11 illustrates a flow diagram of the main operational steps of a method according to one possible example of the invention.

The main operational steps of one possible example of a method according to the invention will now be described with reference to FIG. 11, keeping in mind that the reference data in the form of calibration curves shown in FIGS. 7A–7B is previously provided by applying measurements to different patients.

The condition of artificial kinetics is created (step 20), for example by applying a single occlusion-release mode. To this end, the over-systolic pressure of about 220 mmHg is applied to the patient's finger and maintained during a certain time period (generally from several seconds to several minutes). Then, the measuring unit is actuated (step 22) to illuminate the measurement location by light beams of different wavelengths during the state C, when the changes of relative light transmission are monotonous (time-dependent) and positive, and to detect light components coming from the fingertip. During this measurement session, whose duration may consist 5 sec, the control unit operates to maintain the cuff in its squeezed position. For example, eight wavelengths $\lambda_1-\lambda_8$ above can be used. Generally, the number of wavelengths is such as to enable the determination of RGF and, preferably, the simultaneous determination of various blood parameters of a specific patient.

Thereafter, the control unit operates the pressuring assembly (step 24) to release the over-systolic pressure. The squeezing action of the cuff is ceased, and after a short delay (about 0.5 sec) the blood flow gradually increases during approximately 5 sec. At this stage, the control unit actuates a further measurement session (step 26) to be carried out at the state D of the transitional blood flow. The light sources continue to illuminate the fingertip, but the squeezing is halted. The detectors, being synchronized by the control unit, detect light signals coming from the fingertip, and the digital output is received at the control unit.

Thus, measured data in the form of light responses $T_1(t)-T_8(t)$ as the functions of time corresponding to the wavelengths $\lambda_1-\lambda_8$ of incident light, respectively, is obtained (step 28). The measured data is processed (step 30) to calculate that RGF parameter (e.g., cut-off wavelength) which fits the calibration curve(s) to be used for determining the blood parameter(s), and to calculate at least one other parameter (e.g., parametric slope)—step 32. The corresponding calibration curve or curves are then utilized for determining one or more blood parameters (step 34).

It should also be noted that the above technique refers to each of the following cases:

(1) time variations of the light responses are measured within a time period that lasts from the pre-occlusion state till the post-occlusion state, i.e., the measurements start at a normal blood flow state, continue during the period of the temporary cessation blood flow state, and end up after the transitional blood flow state (excluding two short time periods when the application of the over-systolic pressure is mechanically started and ceased causing non-monotonic fluctuations);

(2) all the measurements are taken during the period including the temporary cessation and the transitional blood flow states (similarly, excluding the short time periods when the application of the over-systolic pressure is started and ceased);

(3) measurements are carried out only during the release state with the corresponding transitional process.

It has been found by the inventors, that the allowed duration of the temporary blood cessation state (state C) depends on many factors, and can be observed approximately between the moments of 0.5 sec and more than a minute from applying the over-systolic pressure. If the changes of the light response (i.e., transmission or reflection) exceed 15–20%, the duration of the temporary blood cessation state may be shortened to 2–3 sec, after which the over-systolic pressure should be released.

The above data is given for measurements effected on a fingertip constituting a fleshy medium. Of course, deviations are possible, if other body parts are considered (such as palms or toes) in which it is easy to achieve a temporary cessation of the blood flow. The parameters of interest may be ESR, oxygen saturation, and/or the concentration of glucose, hemoglobin, drugs, cholesterol, etc.

Those skilled in the art will readily appreciate that various modifications and changes may be applied to the preferred embodiment of the invention as hereinbefore exemplified without departing from its scope defined in and by the appended claims.

What is claimed is:

1. A non-invasive method of optical measurements for determining at least one desired biochemical parameter of patient's blood, the method comprising the steps of:

(a) providing reference data indicative of the at least one desired blood parameter as a function of at least two measurable parameters, wherein one of said at least two measurable parameters is derived from scattering spectral features of a patient's blood perfused fleshy medium and another of said at least two measurable parameters is indicative of artificial kinetics of optical characteristics of the patient's blood perfused fleshy medium;

(b) creating a condition of artificial kinetics and maintaining this condition for a certain time $t_C$, the condition of artificial kinetics being created by causing blood flow modulations imposed from upstream of a measurement location with respect to a normal blood flow direction in the medium and substantially not affecting a blood volume at the measurement location, said blood flow modulations resulting in dynamical changes of light response at the measurement location to incident light;

(c) applying optical measurements to the measurement location during a predetermined time period t including said certain time $t_C$ by illuminating the measurement location with incident light beams of different wavelengths in a red-NIR range, detecting the light responses T of the medium, and generating measured data in a form of time evolutions of the light responses T(t) of the medium at said measurement location for said different wavelengths, respectively, during said predetermined time period t;

(d) analyzing the measured data for determining calculated values of said at least two measurable parameters; and (e) utilizing the calculated values and said reference data for determining a resulting value of the at least one desired blood parameter.

2. The method according to claim 1, wherein said certain time $t_c$ during which the condition of the artificial kinetics is maintained is such as to enable to follow resulting change in the optical characteristics of the medium with sufficient signal-to-noise ratio.

3. The method according to claim 1, wherein said condition of artificial kinetics is created by applying an over-systolic pressure to the patient's blood perfused fleshy medium with a normal blood flow at a location upstream of said measurement location with respect to the direction of normal blood flow, thereby creating a state of temporary blood flow cessation at said measurement location, said state of temporary blood flow cessation being maintained during a certain cessation time.

4. The method according to claim 3, wherein the application of the over-systolic pressure is carried out with a single occlusion-release mode, said certain time $t_c$ being the cessation time.

5. The method according to claim 3, wherein the application of the over-systolic pressure is carried out with a multiple occlusion-release mode.

6. The method according to claim 3, wherein said cessation time is insufficient for irreversible changes in the fleshy medium, and lasts from one second to one minute or more.

7. The method according to claim 1, wherein the time period t during which the measurements are carried out includes both a time period when natural kinetics of the optical characteristics of the medium exists and the time period when the artificial kinetics of the optical characteristics of the medium exists.

8. The method according to claim 1, wherein said reference data is in the form of calibration curves, each curve being in the form of said another of said at least two measurable parameters as a function of values of said at least one desired blood parameter, different calibration curves corresponding to different values of said one of the at least two measurable parameters.

9. The method according to claim 1, wherein the determination of said one of the at least two measurable parameters comprises:

determining a ratio $\Delta(\log T)/\Delta t$ as a function of wavelength $\lambda$ obtained from the measured data T(t) with the different wavelengths, $\Delta t$ being a preset time interval of said predetermined period of time t; and determining a Roulaue Geometry Factor (RGF) as a cut-off wavelength $\lambda_0$ corresponding to the following condition: $\Delta(\log T)/\Delta t=0$.

10. The method according to claim 9, wherein said preset time interval $\Delta t$ is an asymptotic time interval characterized by relatively slow changes of the light response with time, as compared to an initial time interval of said predetermined period of time.

11. The method according to claim 1, wherein the determination of said one of the at least two measurable parameters comprises:

determining a ratio $\Delta T/\Delta t$ as a function of wavelength $\lambda$ obtained from the measured data T(t) with the different wavelengths, $\Delta t$ being a preset time interval of said predetermined period of time t; and determining a Roulaue Geometry Factor (RGF) as a cut-off wavelength $\lambda_0$ corresponding to the following condition: $\Delta T/\Delta t=0$.

12. The method according to claim 11, wherein said preset time interval $\Delta t$ is an asymptotic time interval characterized by relatively slow changes of the light response with time, as compared to an initial time interval of said predetermined period of time.

13. The method according to claim 1, wherein the determination of said another of the at least two measurable parameters comprises the step of:

determining in the state of artificial kinetics a relation between a first light response of the medium illuminated with one of said different wavelengths and a second light response of the medium illuminated with another wavelength from said different wavelengths, the two wavelengths being selected in accordance with said desired blood parameter to be determined.

14. The method according to claim 13, wherein said relation is determined as a parametric slope in a line representing said first light response as a function of the second light response.

15. The method according to claim 1, wherein said at least one desired biochemical blood parameter is concentration of hemoglobin.

16. The method according to claim 1, wherein said at least one desired blood parameter is oxygen saturation.

17. The method according to claim 1, wherein said at least one desired blood parameter is Erythrocyte Sedimentation Rate (ESR).

18. The method according to claim 1, wherein said at least one desired blood parameter is Erythrocyte Aggregation Rate (EAR).

19. An apparatus for non-invasive optical measurements of at least one desired biochemical parameter of patient's blood, the apparatus comprising:

(i) a measuring unit operable for applying optical measurements to a patient's blood perfused fleshy medium at a measurement location by illuminating the measurement location with incident light beams of different wavelengths, detecting light responses T of the medium corresponding to the different wavelengths of the incident light, respectively, and generating data indicative thereof;

(ii) a pressurizing assembly operable for applying pressure to the patient's blood perfused fleshy medium at a location upstream of the measurement location with respect to a normal blood flow direction in the medium, so as to create a condition of artificial kinetics of optical characteristics of the medium substantially without affecting a blood volume at the measurement location, and to maintain said condition for a certain time $t_C$;

(iii) a control unit connectable to the measuring unit and to the pressurizing assembly for synchronizing the operation thereof, the control unit comprising;

(iv) a memory for storing reference data indicative of said at least one desired blood parameter as a function of at least two measurable parameters, wherein one of said at least two parameters is derived from scattering spectral features of the medium, and said another of at least two measurable parameters is indicative of the artificial kinetics of the optical characteristics of the patient's blood perfused fleshy medium; and (v) a data acquisition and processing utility coupled to output of the measuring unit for receiving and analyzing the data indicative of the light responses T detected during the certain time $t_C$ to determine measured data in a form of time evolutions of light responses T(t) of the medium at said measurement location corresponding to the different wavelengths of the incident light, respectively, and to utilize said measured data and reference data to determine said at least one desired blood parameter.

20. The apparatus according to claim 19, wherein the pressurizing assembly is accommodated so as to apply an over-systolic pressure to said location upstream of said measurement location, so as to create a state of blood flow cessation at the measurement location inducing said condition of the artificial kinetics.

21. A non-invasive method of optical measurements for determining at least one desired biochemical parameter of patient's blood, the method comprising the steps of:

(a) providing reference data indicative of the at least one desired blood parameter as a function of at least two measurable parameters, wherein one of said at least two measurable parameters is derived from scattering spectral features of a patient's blood perfused fleshy medium, and another measurable parameter is indicative of artificial kinetics of optical characteristics of the patient's blood perfused fleshy medium;

(b) creating a condition of artificial kinetics of optical characteristics of the medium, and maintaining this condition for a certain time $t_C$, the condition of artificial kinetics being created and maintained by applying an over-systolic pressure with a multiple occlusion-release mode to the patient's blood perfused fleshy medium with a normal blood flow at a location upstream of a measurement location with respect to direction of the normal blood flow, thereby creating a state of temporary blood flow cessation at said measurement location during a certain cessation time;

(c) illuminating the measurement location with incident light beams of different wavelengths in a red-NIR range, detecting light responses T of the medium, and generating measured data in the form of time evolutions of the light responses T(t) of the medium at said measurement location for said different wavelengths, respectively, during a predetermined time period t including said certain time $t_C$;

(d) analyzing the measured data for calculating values of said at least two measurable parameters; and (e) utilizing the calculated values and said reference data for determining a resulting value of the at least one desired blood parameter.

22. A non-invasive method of optical measurements for determining at least one desired biochemical parameter of patient's blood, the method comprising the steps of:

(a) providing reference data presenting said at least one desired blood parameter as a function of at least two measurable parameters, wherein one of said at least two measurable parameters is derived from scattering spectral features of a patient's blood perfused fleshy medium, and another measurable parameter is indicative of artificial kinetics of the optical characteristics of the patient's blood perfused fleshy medium, the reference data being in a form of calibration curves, each curve being in a form of said another measurable parameter as a function of values of said at least one desired blood parameter, different calibration curves corresponding to different values of said one of the at least two measurable parameters;

(b) creating a condition of artificial kinetics of the optical characteristics of the medium and maintaining this condition for a certain time $t_C$, the condition of artificial kinetics being created by causing blood flow modulations in the medium imposed from upstream of a measurement location with respect to a normal blood flow direction in the medium and substantially not affecting a blood volume at the measurement location, said blood flow modulations resulting in dynamical changes of light response of the measurement location to incident light;

(c) illuminating the measurement location with incident light beams of different wavelengths in a red-NIR range, detecting light responses T of the medium, and generating measured data in the form of time evolutions of the light responses T(t) of the medium at said measurement location for said different wavelengths, respectively, during a predetermined time period t including said certain time $t_C$;

(d) analyzing the measured data for calculating values of said at least two measurable parameters; and (e) utilizing the calculated values and said reference data for determining a resulting value of the at least one desired blood parameter.

23. The method according to claim 22, wherein said biochemical blood parameter is one of concentration of hemoglobin, concentration of glucose, cholesterol, oxygen saturation, Erythrocyte Sedimentation Rate (ESR), and Erythrocyte Aggregation Rate (EAR).

24. A non-invasive method of optical measurements for determining at least one desired parameter of patient's blood, the method comprising the steps of:
(a) providing reference data indicative of the at least one desired blood parameter as a function of at least two measurable parameters, wherein one of said at least two measurable parameters is derived from scattering spectral features of a patient's blood perfused fleshy medium, and said another measurable parameter is indicative of artificial kinetics of optical characteristics of the patient's blood perfused fleshy medium;
(b) creating a condition of artificial kinetics of the optical characteristics of the medium and maintaining this condition for a certain time $t_C$, the condition of artificial kinetics being created by causing blood flow modulations in the medium imposed from upstream of a measurement location with respect to a normal blood flow direction in the medium and substantially not affecting a blood volume at the measurement location, said blood flow modulations resulting in dynamical changes of light response of the measurement location to incident light;
(c) illuminating the measurement location with incident light beams of different wavelengths in a red-NIR range, detecting light responses T of the medium, and generating measured data in a form of time evolutions of the light responses T(t) of the medium at said measurement location for said different wavelengths, respectively, during a predetermined time period t including said certain time $t_C$;
(d) analyzing the measured data for calculating values of said at least two measurable parameters, said one of the at least two measurable parameters being a Roulaue Geometry Factor (RGF), the determination of the RGF comprising determining a ratio $\Delta(\log T)/\Delta t$ as a function of wavelength $\lambda$ obtained from the measured data T(t) with the different wavelengths, $\Delta t$ being a preset time interval of said predetermined period of time t, and determining the RGF as a cut-off wavelength $\lambda_0$ corresponding to the following condition: $\Delta(\log T)/\Delta t=0$; and
(e) utilizing the calculated values and said reference data for determining a resulting value of the at least one desired blood parameter.

25. The method according to claim 24, wherein said preset time interval $\Delta t$ is an asymptotic time interval characterized by relatively slow changes of the light response with time, as compared to an initial time interval of said predetermined period of time.

26. A non-invasive method of optical measurements for determining at least one desired parameter of patient's blood, the method comprising the steps of:
(a) providing reference data indicative of the at least one desired blood parameter as a function of at least two measurable parameters, wherein one of said at least two measurable parameters is derived from scattering spectral features of a patient's blood perfused fleshy medium, and another of said at least two measurable parameters is indicative of artificial kinetics of optical characteristics of the patient's blood perfused fleshy medium;
(b) creating a condition of artificial kinetics of optical characteristics of the medium and maintaining this condition for a certain time $t_C$, the condition of artificial kinetics being created by causing blood flow modulations in the medium imposed from upstream of a measurement location with respect to a normal blood flow direction in the medium and substantially not affecting a blood volume at the measurement location, said blood flow modulations resulting in dynamical changes of light response of the measurement location to incident light;
(c) illuminating the measurement location with incident light beams of different wavelengths in a red-NIR range, detecting light responses T of the medium, and generating measured data in the form of time evolutions of the light responses T(t) of the medium at said measurement location for said different wavelengths, respectively, during a predetermined time period t including said certain time $t_C$;
(d) analyzing the measured data for calculating values of said at least two measurable parameters, said one of at least two measurable parameters being a Roulaue Geometry Factor (RGF), the determination of the RGF comprising determining a ratio $\Delta T/\Delta t$ as a function of wavelength $\lambda$ obtained from the measured data T(t) with the different wavelengths, $\Delta t$ being a preset time interval of said predetermined period of time t, and determining the RGF as a cut-off wavelength $\lambda_0$ corresponding to the following condition: $\Delta T/\Delta t=0$; and
(e) utilizing the calculated values and said reference data for determining a resulting value of the at least one desired blood parameter.

27. A method of non-invasive optical measurements of at least one desired parameter of patient's blood, the method comprising the steps of:
(a) operating a pressurizing assembly to apply oversystolic pressure to a location on a patient's blood perfused fleshy medium with a normal blood flow upstream of a measurement location with respect to the normal blood flow direction in the medium, and to maintain the pressure during a certain time period, to thereby create a condition of artificial kinetics of optical characteristics of the medium at the measurement location characterized by a temporary blood flow cessation state at the measurement location, thereby causing dynamical changes of a light response of the medium at the measurement location to incident radiation, the intensity of the light response signal changing by at least 20%;
(b) operating a measuring unit to apply optical measurements to said measurement location during a time period including said certain time period, by illuminating the measurement location with incident light beams of different wavelengths in a red-NIR range and detecting light responses T of the medium to said different wavelengths, respectively, thereby obtaining measured data in the form of time evolutions of the light responses T(t) of the medium at said measurement location for said different wavelengths, respectively;
(c) analyzing the measured data for calculating values of at least two measurable parameters, wherein one of said at least two measurable parameters is derived from scattering spectral features of the patient's blood perfused fleshy medium, and another of said at least two measurable parameters is indicative of artificial kinetics of the optical characteristics of the patient's blood perfused fleshy medium; and
(d) utilizing the calculated values and predetermined reference data for determining a resulting value of the at least one desired blood parameter, said predetermined reference data being indicative of the at least one desired blood parameter as a function of said at least two measurable parameters.

* * * * *